(12) United States Patent
Weber et al.

(10) Patent No.: US 6,524,250 B1
(45) Date of Patent: Feb. 25, 2003

(54) FAT LAYER THICKNESS MAPPING SYSTEM TO GUIDE LIPOSUCTION SURGERY

(75) Inventors: Paul J. Weber, Ft. Lauderdale, FL (US); Luiz B. Da Silva, Danville, CA (US); Alexander M. Rubenchik, Livermore, CA (US)

(73) Assignee: Pearl Technology Holdings, LLC, Clearwater, FL (US)

( * ) Notice: Subject to any disclaimer, the term of this patent is extended or adjusted under 35 U.S.C. 154(b) by 0 days.

(21) Appl. No.: 09/664,943

(22) Filed: Sep. 19, 2000

(51) Int. Cl.[7] ................................................. A61B 8/00
(52) U.S. Cl. ........................................ 600/439; 600/449
(58) Field of Search ................................. 600/437, 440, 600/443, 447, 449, 459; 73/597, 599

(56) References Cited

U.S. PATENT DOCUMENTS

| | | | | |
|---|---|---|---|---|
| 5,060,652 A | * | 10/1991 | Umemura et al. | 600/447 |
| 5,353,796 A | * | 10/1994 | Schroeder et al. | 600/437 |
| 5,685,307 A | * | 11/1997 | Holland et al. | 600/437 |
| 5,793,879 A | * | 8/1998 | Benn et al. | 382/110 |
| 5,941,825 A | * | 8/1999 | Lang et al. | 600/440 |

* cited by examiner

Primary Examiner—Francis J. Jaworski
(74) Attorney, Agent, or Firm—John P. Wooldridge

(57) ABSTRACT

A device is described that can be easily used by surgeons to measure and monitor changes before, during, and after a liposuction procedure and assist in producing symmetrical body contours. The device comprises a remote control and data processing unit, a handheld ultrasound transducer, a display monitor and means for marking anatomical points to be measured.

38 Claims, 6 Drawing Sheets

FAT LAYER THICKNESS MAPPING SYSTEM TO GUIDE LIPOSUCTION SURGERY

BACKGROUND OF THE INVENTION

1. Field of the Invention

The present invention relates to the field of cosmetic surgery generally and specifically to liposuction and soft-tissue plastic surgery. More particularly, the invention relates to a device and method for measuring soft tissue thickness with a handheld apparatus utilizing ultrasound. This device can be easily employed to monitor changes in adipose tissue during a liposuction surgical procedure.

2. Description of Related Art

Liposuction, also known as liposculpture, lipoplasty or suction lipectomy, is a technique to remove stubborn fat deposits that won't respond to dieting and exercise. Liposuction was introduced to the United States in the early 1980's and has since grown in popularity. In a liposuction procedure, a very small incision is made in the skin and a cannula, i.e., a thin, smooth, hollow, blunt, surgical suction rod is inserted. The cannula is connected to a vacuum source with a suction tube and the fat is sucked out leaving the skin, muscle, nerves and blood vessels intact. This procedure allows the surgeon to sculpt and improve body contour with minimal pain and scaring. Through a liposuction procedure fat cells are permanently removed and since fat cells are not thought to regenerate, body contour improvement should be permanent Typically, the amount of fat to be removed is determined by the surgeon by feeling and pinching the skin throughout the surgical procedure. Even with a highly skilled surgeon, variations from the ideal results are possible. While complications are rare they can include uneven skin surface, bleeding, infection, discoloration, fluid accumulation beneath the skin, numbness and scarring.

In an effort to avoid uneven skin surface and achieve proportional body shaping it would be advantageous to accurately measure the adipose tissue thickness before, during and after a liposuction or other soft-tissue plastic surgical procedure. This would aid in maintaining consistency in the areas in which the liposculpture is being preformed.

It is difficult to directly and accurately measure objects that include layers of different compositions (e.g., skin, muscle and bone). With regard to measuring body adipose tissue layers, skin calipers can be used. A measurement is taken by an operator pinching a subject's skin and measuring the thickness of the skin fold with the calipers. Various equations are used to predict body density and the percent of body adipose tissue (American College of Sports Medicine (ACSM) "Guidelines For Exercise Testing And Prescription", 53–63 (1995)). However, there are many drawbacks to this form of adipose tissue measurement. These measurements are heavily dependent on the operator, and errors and variations frequently occur. Skin fold calipers can only provide an estimate of tissue thickness and are not particularly useful for liposuction procedures.

Another means of determining body density and estimating percent body adipose tissue is a generalized measurement hydrostatic weighing. Hydrostatic weighing requires the subject to be completely immersed in water. This method of measurement could only be employed before and after a liposuction procedure, which would be impractical and costly when the goal is to monitor adipose tissue changes during the surgery. Additionally, the surgeon performing liposculpture and most surgical contouring procedures requires localized measurements. Maintenance of a sterile field is problematic with such a method.

It becomes apparent that a method and apparatus is needed to efficiently and accurately measure adipose tissue before, during, and after a liposuction or soft-tissue plastic surgery procedure. U.S. Pat. No. 5,941,825 dated October 1996 by Lang et al., recognized that ultrasound could be utilized to conveniently and cost effectively measure layer thickness in an object The present invention introduces the use of ultrasound in a hand held device to measure fat tissue thickness in a human. WO 99/65395 dated December 1999 by Lang et al., builds on the previously referenced patent by using anatomical landmarks to measure changes in body adipose tissue. The aim of these two patents is to measure adipose tissue changes over time as a result of diet and exercise.

There is a need for an accurate, convenient, cost effective means and apparatus to measure adipose tissue thickness before, during and after a liposuction or soft-tissue plastic surgical procedure that would provide a high probability of success without producing undesirable side effects yet be conveniently kept sterile when necessary. In addition, a simple device to accurately measure localized body tissue layer thickness could be useful to monitor and map the local or regional effects of dietary changes and diet. The present invention fulfills this need, and further provides related advantages.

SUMMARY OF THE INVENTION

It is an object of the present invention is to provide a system for accurately measuring tissue layer thickness before, during and after a liposuction or soft-tissue plastic surgical procedure.

Another object of the present invention is to provide a system to easily create body maps of tissue layer thickness to monitor the effects of exercise or diet.

These and other objects will be apparent to those skilled in the art based on the teachings herein.

In particular, the system can be used to produce a map of the fat (or adipose) or soft tissue thickness at key anatomical points. These measurements can be monitored and compared during a liposuction procedure to guide the surgeon. In one embodiment, the device comprises a remote control and data processing unit, a handheld ultrasound transducer, a monitor to display the information to the user and means to mark anatomical points of interest.

In normal use, the user would mark key anatomical points at the beginning of the procedure. The points could be marked and coded directly on the skin with a water resistant marking pen. In this mode of operation, the point of measurement would be noted by the user and input into the control system. Alternatively, key anatomical points could be marked by placing a series of encoded stickers or stamps. The stickers could be numerically labeled, color-coded or electrically coded. If coded, sensors in the handheld transducer could automatically detect the sticker code and record the location of the measurement automatically. Another technique for registering the measurement points is to use a tracking mechanism similar to that used in electronic track balls or computer mice. In this technique, the user moves the device along a predefined or marked track on the skin that is recorded by the control tunit. The control unit generates a map and records the location of each point of measurement.

The handheld ultrasound transducer uses a single or a plurality of ultrasound generating and detection elements to obtain an effective A-Scan ("Ultrasound in Medicine" Ed. F.

A. Duck, A. C. Baker, H. C. Starritt (1997)) of the tissue structure directly below the transducer. The A-scan will show strong reflections at the interface between the various layers i.e., skin, fat, muscle and bone. Strong ultrasound reflections occur at the interfaces due to impedance mismatch between the various materials. The A-scan signal can be analyzed by the control unit to determine the thickness of the various tissue layers (skin, fat, muscle). During and immediately after the procedure the fat layer may have a mixture of loose fat and water. The reflected ultrasound signal in this non-homogeneous layer will be different than the normal fat layer. Analysis of the reflected signal amplitude in this layer can be used to calculate an effective fat layer thickness. In addition, the ultrasound transducer can operate at two or more frequencies. Since the scattered signal scales strongly with the ultrasound wavelength the ratio of scattered signal at different frequencies can be used to estimate the water-fat mixture.

In one embodiment, the transducer is not connected by a wire or cable to the control unit The transducer and control unit communicate through a wireless means (e.g., RF communication). The advantage of this is that the control unit and display can be far away from the sterile surgical field. RF communication eliminates having to cover the control unit and cable with sterile bags. In addition, in this embodiment the ultrasound transducer is powered by batteries, which reduce the electrical hazard concern.

The remote control unit acquires the data from the handheld transducer and analyzes the data to produce a table of tissue thickness parameters for all the anatomical points. This data can be displayed in a tabulated list or a color-coded anatomical map that can be easily interpreted by the surgeon. Additionally, the display can show the change in the fat layer thickness during the course of the liposuction procedure. The user can control the display and function of the control unit through a keyboard/mouse interface or touch screen.

Using this system, the surgeon will be more able to accurately control liposuction surgery. This will improve procedure outcome by reducing the chances of producing non-symmetric results.

In addition, to being used in liposuction surgery, the present invention can be used to easily create maps of tissue layer thickness. This can be used to monitor changes in fat layer thickness as a function of dietary changes or exercise.

Other objects and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

Figure 1:
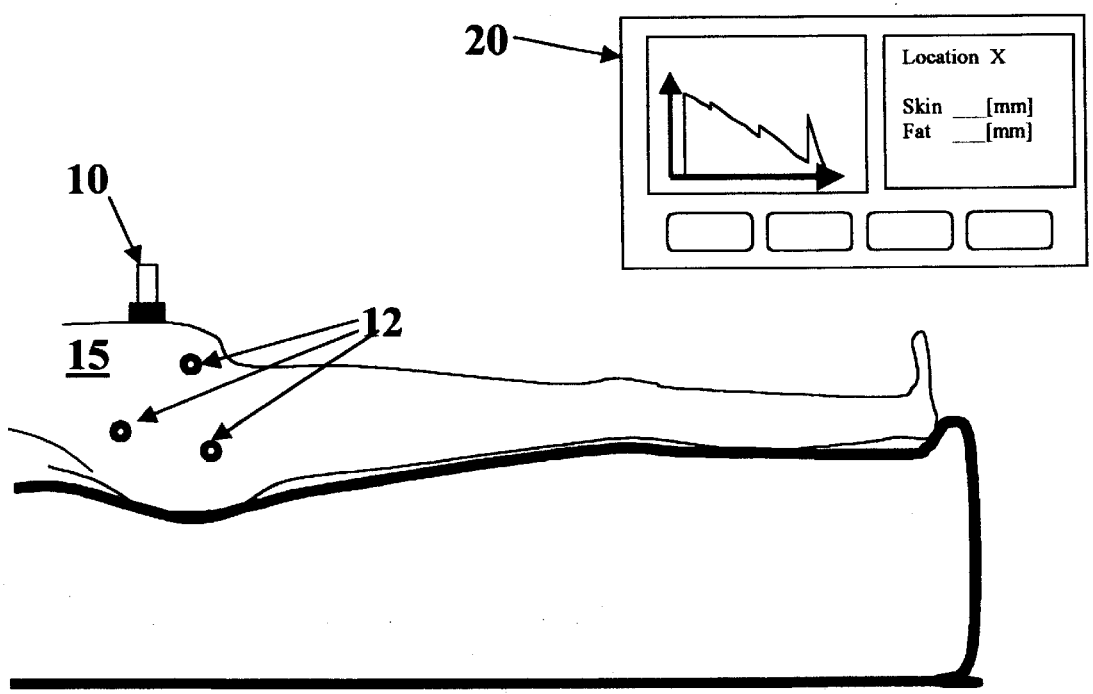
FIG. 1 shows how the device would be used to measure tissue layer thickness in one embodiment of the present invention.

The object of the present invention is to provide a system for accurately measuring tissue layer thicknesses before, during and after a liposuction procedure. In particular, the system can be used to produce a map of the fat (or adipose) tissue thickness at key anatomical points. These measurements can be monitored and compared during a liposuction procedure to guide the surgeon. In one embodiment, the device comprises a remote control and data processing unit, a handheld ultrasound transducer, a monitor to display the information to the user and means to mark anatomical points of interest FIG. 1 illustrates how the present invention would be used to measure the local tissue structure. The measuring device 10 is placed on the skin 15 at a point of interest that has been previously marked. When activated, an ultrasound signal is transmitted into the tissue and the return signal collected. The collected signal is than communicated either through a direct wire connection or some wireless means, such as, RF, acoustic, or microwave to the remote control unit 20. The control unit 20 displays the recorded waveforms and calculated thickness of relevant layers. In addition, the control unit 20 stores the waveforms and information about the location of the measurement so that the user can easily monitor changes during the liposuction procedure. In normal use the measuring device would be applied at multiple key anatomical points, e.g., at points 12, before starting the liposuction procedure. The surgeon would than use the measurements to guide the procedure and perform further measurements during the procedure to achieve the desired reduction in adipose tissue thickness.

Figure 2:
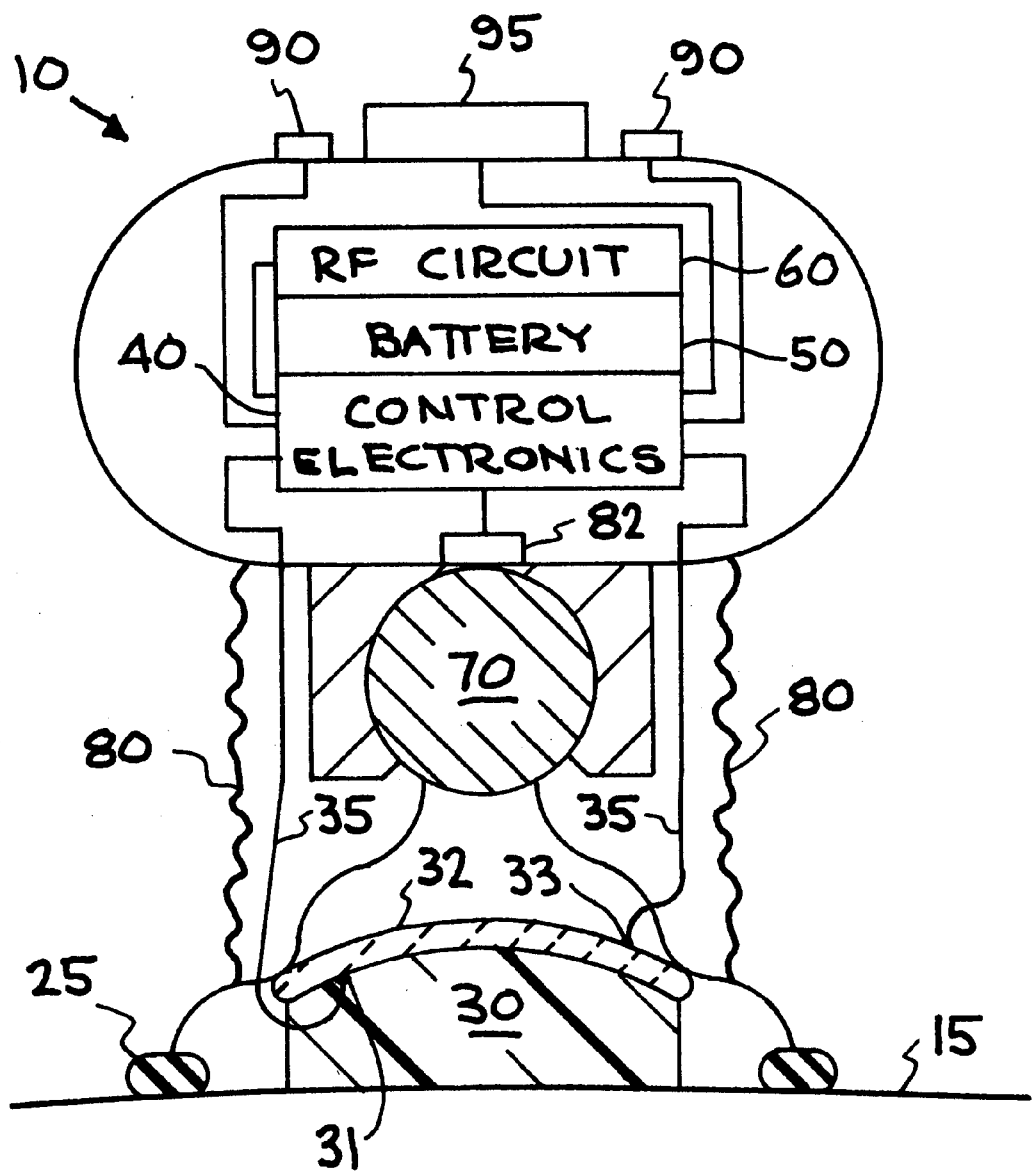
FIG. 2 shows a sectional view taken through the handheld ultrasound device of FIG. 1.

FIG. 2 shows a detailed cross-sectional view of the handheld ultrasound measuring device 10. The device consists of an acoustic matching layer 30 that efficiently couples the ultrasound pulse from the generating element 32 to the tissue 15. The acoustic matching layer 30 can be an acoustic gel, hydro gels, or a variety of low density polymers commonly used in ultrasound imaging. The ultrasound generation and detection element 32 is a curved piezoelectric transducer that controls the electrical signal delivered by wires 35 to the electrodes 31 and 33.

For this device, the operating frequency of the transducer will typically be in the range of 500 kHz to 10 MHz. The higher frequencies have higher spatial resolution but suffer from high tissue attenuation, which limits the thickness of tissue that can be measured. In addition, it is sometimes beneficial to operate the ultrasound transducer at two different frequencies. Since the scattered signal scales strongly with the ultrasound wavelength, the ratio of scattered signal at two frequencies can be used to determined tissue properties.

A curved transducer may be used to provide a weakly focused beam that measures properties over a less than 5 mm diameter region. A small diameter reduces the blurring of layer boundaries due to non-planar layer contours. The transducer is used to both generate the ultrasound pulse and measure the time history of the return acoustic signal. The collected time history signal is a measurement of the back-scattered signal as a function of depth averaged over the ultrasound beam area. The control electronics collect and digitize the signal for further display and analysis. For additional information on transducer design and operation refer to "The Physics of Medical Imaging" Ed. Steve Webb (1988) incorporated herein by reference, and "Ultrasound in Medicine" Ed. F. A. Duck, A. C. Baker, H. C. Starritt (1997)

incorporated herein by reference. See also U.S. Pat. No. 5,699,806, titled "Ultrasound System With Nonuniform Rotation Corrector" incorporated herein by reference.

In the embodiment shown in FIG. 2, all the control electronics 40 are in the measuring device 10 powered by a battery 50 and the signal is transmitted by wireless communication by an RF circuit 60 to a remote control unit This has the added advantage of eliminating the need for electrical wires that cross into the sterile surgical field. One possible wireless communication protocol is blue tooth technology currently being used in a variety of devices. Bluetooth refers to a short-range radio technology aimed at simplifying communications among Net devices and between devices and the Internet. It also aims to simplify data synchronization between Net devices and other computers. Products with Bluetooth technology must be qualified and pass interoperability testing by the Bluetooth Special Interest Group prior to release. The Bluetooth 1.0 specification consists of two documents: the Foundation Core, which provides design specifications, and the Foundation Profile, which provides interoperability guidelines. Bluetooth's founding members include Ericsson, IBM, Intel, Nokia and Toshiba. Alternatively, as in most ultrasound imaging systems the control electronics are separate from the transducer device and connected by a multi-wire cable.

The measuring device 10 can include a ball joint segment 70 with a flexible cover 80 to ensure that the transducer plane is parallel to the. tissue surface. This is important to ensure that all measurements are made approximately along the same imaging axis to improve reproducibility. In addition, a soft edge 25 minimizes tissue deformation.

The device 10 is activated and controlled by using buttons 90. In addition to the main control unit screen, an optional display 95 on the device shows the device status and key parameters. A measurement can be initiated when the user touches button 90. Alternatively, the device can be put into an automatic state in which a measurement is made when the contact switch 82 is closed. Switch 82 closure will occur when the device 10 is pressed up against the tissue and a minimal pressure applied. It is important to minimize the required pressure in order to reduce tissue deformation that would perturb the measurement.

In order to enter the sterile field, the measurement device 10 can be placed in a sterile plastic bag. Alternatively, the device 10 could be inserted into a disposable plastic container with an acoustic matching bottom segment.

In order to compare measurements during the liposuction procedure, it is important that the location of each measurement is recorded and that the measuring device is placed within a few mm of the original position. Several possible techniques can be used to automate this process. In one embodiment, the user places encoded sterile stickers on all the desired positions. The stickers could be circular with a diameter approximately equal to the measuring device 10 diameter. To make a measurement, the user aligns the measuring device on the sticker and collects a measurement. In one example, the stickers are encoded with a simple number that is read and entered into the control unit or the handheld transducer by the user. Alternatively, the sticker could be color-coded. In this case, the measurement device would include a light source and a plurality of filtered light detectors to measure the sticker color and automatically determine the sticker code. A variety of other encoding techniques are possible, including capacitive, resistive or, magnetic.

In another embodiment, the user uses a stamp or marker to place a circle or cross on the tissue along with a number for easy reference. In this case, the user enters the location number for each measurement directly into the control unit This process can be automated in the case where the measurements are made in sequence by having the control unit automatically increment the location number.

In another embodiment, a tracking mechanism similar to that used in electronic track balls or computer mice is used to determine the measurement location. In this embodiment, the user moves the device along a predefined or marked track on the skin and the data along this track is recorded by the control unit. The control unit generates a map and records the location of each point of measurement.

Figure 3:
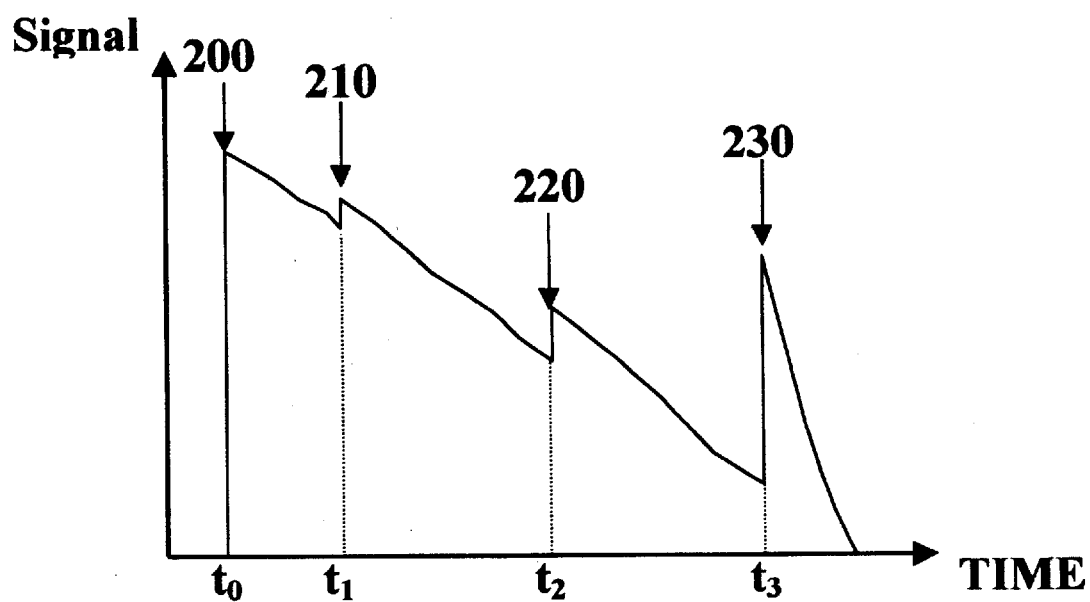
FIG. 3 is a graphic illustration of the signal recorded by the device when applied to skin.

FIG. 3 shows a graphic illustration of a typical measurement signal. The discontinuities at 200, 210, 220 and 230 correspond to the interface between the various tissue layers. The tissues layers are shown as skin surface 200, fat 210, muscle 220 and bone 230. Strong ultrasound reflections occur at the interfaces due to impedance mismatch between the various materials. The time history is converted to thickness by the software by using average sound speeds (c). For example, c~1600 m/s for skin, 1400 m/s for fat, 1600 m/s for muscle, and 3500 m/s for bone (See "Ultrasound in Medicine" Ed. F. A. Duck, A. C. Baker, H. C. Starritt). During and immediately after the liposuction procedure, the fat layer may have a mixture of loose fat and water. The reflected ultrasound signal in this non-homogeneous layer will be different than the normal fat layer. Analysis of the reflected signal amplitude in this layer can be used to calculate an effective fat layer thickness. In addition, the ultrasound transducer can operate at two or more frequencies. Since the scattered signal scales strongly with the ultrasound wavelength, the ratio of scattered signal at different frequencies can be used to estimate the water-fat mixture. The control unit can display the signal and the calculated layer thickness for the layers of interest automatically. In addition, with user input, the control unit can show anatomical maps color-coded with the selected layer thickness or change in layer thickness after the procedure.

Figure 4:
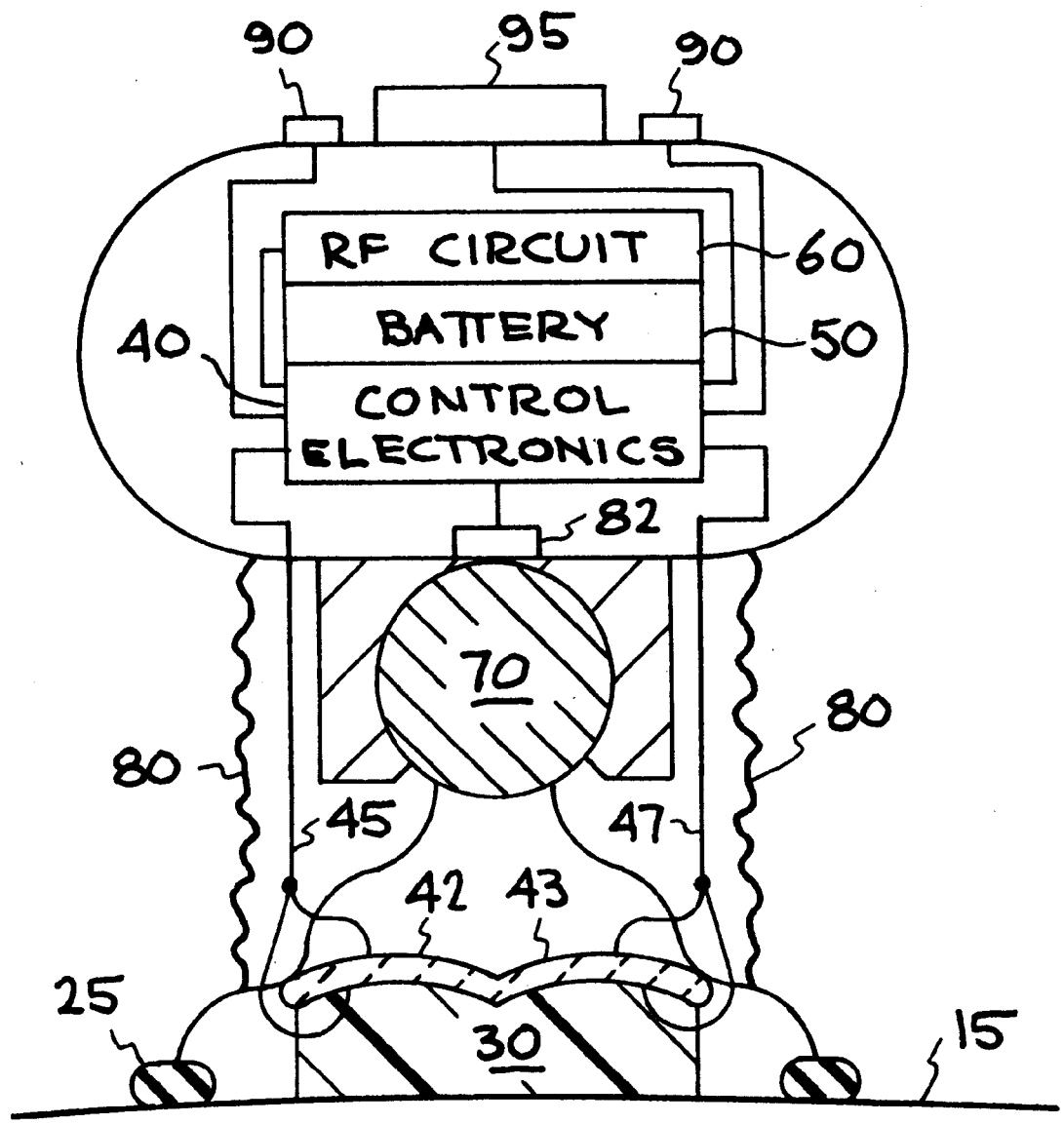
FIG. 4 shows a sectional view of an alternative device that uses multiple ultrasound transducers.

FIG. 4 shows an alternative embodiment that uses two ultrasound transducers. In this embodiment the control electronics 40 activate the two transducers 42, 43 separately through leads 45, 47 to collect two different signals. By processing these two signals by simply averaging or using techniques known in the art it is possible to obtain a more accurate determination of the layer interfaces.

Figure 5:
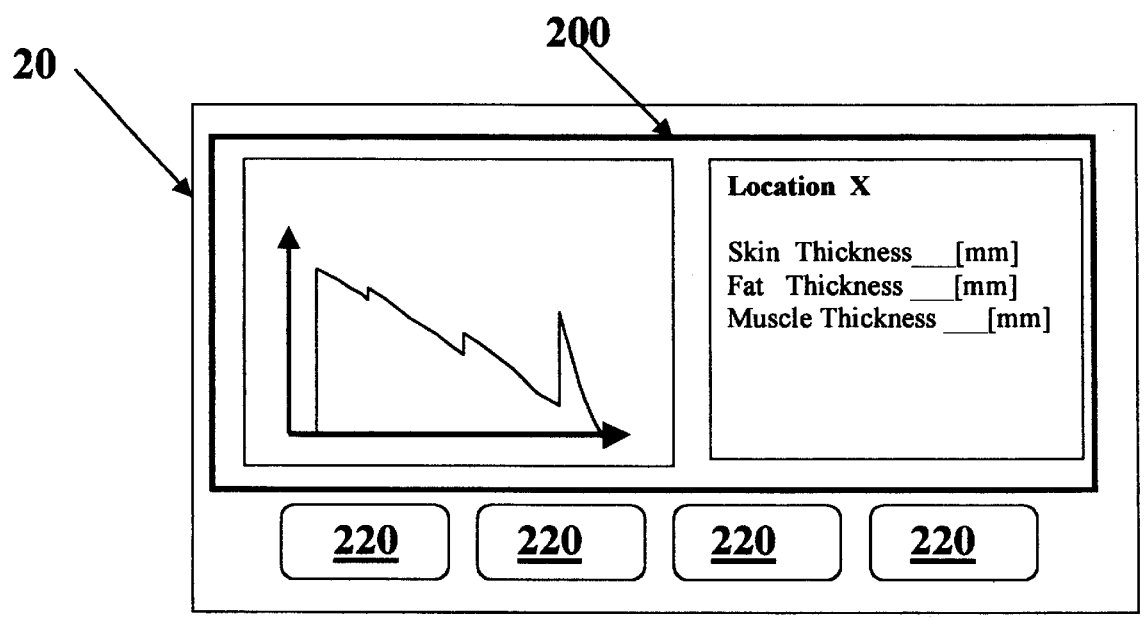
FIG. 5 shows an illustration of the main control unit

FIG. 5 shows an illustration of the main control unit 20. The control unit has a screen 200 and control buttons 220. A menu driven interface is used to input commands and control the system. A keyboard or touch screen interface can also be used for input. The control unit could also simply be a personal or portable computer with an adapter card to communicate with the transducer.

Figure 6:
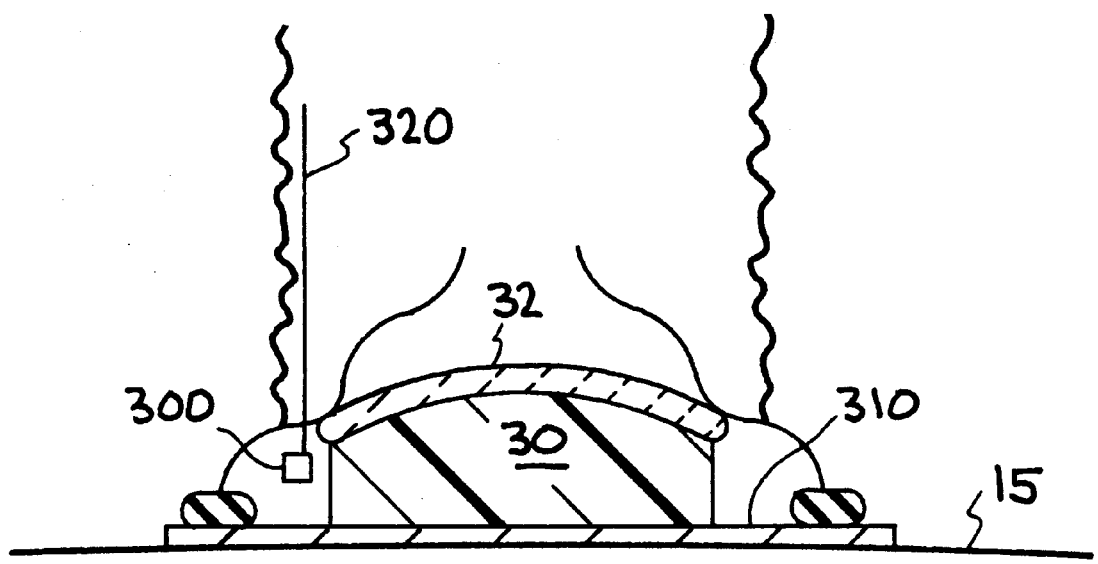
FIG. 6 shows a sectional view of a section of the handheld ultrasound transducer.

FIG. 6 shows how an optical detector 300 can be integrated into the handheld ultrasound transducer to detect the color of the sticker 310. The optical detector 300 can consist of multiple optical sensors each filtered for a different color (for example three sensors with red, green or blue filters). The optical detector 300 is connected to the control electronics 40 by cable 320. The signal in each optical sensor is analyzed by the control unit to determine the sticker color. The number of possible colors increases with the number of sensors used.

The above descriptions and illustrations are only by way of example and are not to be taken as limiting the invention in any manner. One skilled in the art can substitute known equivalents for the structures and means described. The full scope and definition of the invention, therefore, is set forth in the following claims.

We claim:

1. A system for mapping tissue layer thickness, comprising:
   an ultrasound transducer for producing ultrasound energy;
   means for coupling said ultrasound energy to skin;
   means for identifying location of said ultrasound transducer;
   a control unit for controlling said ultrasound transducer and processing data signals received from said ultrasound transducer;
   means for transmitting a signal from said ultrasound transducer to said control unit; and
   means for displaying tissue thickness parameters received from said control unit,
   wherein said control unit comprises software that is adapted to read and analyze data from said ultrasound transducer, wherein said software is adapted to produce a fat thickness map and guide a liposuction procedure.

2. The system of claim 1, wherein said control unit includes control software, wherein said system further comprises means for inputting commands to said control software to control the operation and display of said systems.

3. The system of claim 1, wherein said means for coupling said ultrasound transducer to skin is selected from the group consisting of an acoustic coupling gel, a fluid filled plastic bladder, a hydro gel and a low density polymers.

4. The system of claim 1, wherein said means for transmitting an ultrasound signal is selected from the group consisting of an electrical cable from said transducer to said control unit and wireless means for transmitting said ultrasound signal.

5. The system of claim 4, wherein said means for transmitting an ultrasound signal comprises wireless means for transmitting said ultrasound signal, wherein said wireless means comprises means for RF communication between said ultrasound transducer and said control unit.

6. The system of claim 4, wherein said means for transmitting an ultrasound signal comprises wireless means for transmitting said ultrasound signal, wherein said wireless means comprises means for acoustic communication between said ultrasound transducer and said control unit.

7. The system of claim 4, wherein said means for transmitting an ultrasound signal comprises wireless means for transmitting said ultrasound signal, wherein said wireless means comprises means for microwave communication between said ultrasound transducer and said control unit.

8. The system of claim 4, wherein said means for transmitting an ultrasound signal comprises wireless means for transmitting said ultrasound signal, wherein said wireless means are configured to conform to blue tooth wireless protocol.

9. The system of claim 1, wherein said means for identifying location of said ultrasound transducer comprises means for direct user input into said control unit.

10. The system of claim 9, wherein said means for identifying location of said ultrasound transducer comprises coded stickers for placement on the skin, wherein said coded stickers are encoded with an encoding technique selected from the group consisting of color coding, capacitive coding, resistive coding and magnetic coding.

11. The system of claim 9, wherein said means for identifying location of said ultrasound transducer comprises coded stickers for placement on the skin, wherein said coded stickers comprises a color code, the system further comprising a light source and a plurality of filtered light detectors operatively fixed within said housing and electrically connected to said control unit.

12. A system for mapping tissue layer thickness, comprising:
   an ultrasound transducer for producing ultrasound energy;
   means for coupling said ultrasound energy to skin;
   means for identifying location of said ultrasound transducer;
   a control unit for controlling said ultrasound transducer and processing data signals received from said ultrasound transducer;
   means for transmitting a signal from said ultrasound transducer to said control unit; and
   means for displaying tissue thickness parameters received from said control unit, wherein said means for identifying location of said ultrasound transducer comprises coded stickers for placement on the skin, wherein said system further comprises at least one sensor operatively connected to said control unit and adapted to sense the presence of said coded stickers, wherein said control unit further comprises means for automatically detecting said code.

13. The system of claim 12, wherein said at least one sensor is selected from the group consisting of an optical sensor, a capacitive sensor and a resistive sensor.

14. The system of claim 1, further comprising a handholdable housing, wherein said ultrasound transducer is fixedly and operatively housed within said handholdable housing.

15. The system of claim 14, further comprising a second ultrasound transducer fixedly and operatively housed within said handholdable housing.

16. The system of claim 14, further comprising a plurality of ultrasound transducers fixedly and operatively housed within said handholdable housing.

17. The system of claim 14, further comprising ball joint segment movably and operatively connected between said ultrasound transducer and said handholdable housing.

18. The system of claim 17, further comprises a contact switch between said ball joint segment and said means for responding to control signals received from said control unit, wherein said contact switch is actuated by the application of pressure between said housing and tissue, wherein said contact switch initiates operation of said system.

19. The system of claim 14, wherein said handholdable housing includes a flexible cover to allow adjustment of the orientation of said ultrasound transducer with respect to tissue surface.

20. The system of claim 14, wherein said handholdable housing comprises a soft edge to minimize tissue deformation.

21. The system of claim 14, wherein said handholdable housing comprises means for displaying device status and parameters.

22. The system of claim 1, wherein said means for displaying tissue thickness parameters comprises a monitor.

23. The system of claim 1, further comprising a tracking mechanism operatively connected to said ultrasound transducer, wherein as a user moves said ultrasound transducer on the skin, the position of said transducer is recorded by said control unit, wherein said control unit generates said map and records the location of each point of measurement.

24. The system of claim 23, wherein said tracking mechanism is selected from the group consisting of an electronic track ball and a computer mouse.

25. A system for mapping tissue layer thickness, comprising:
 an ultrasound transducer for producing ultrasound energy;
 means for coupling said ultrasound energy to skin;
 means for identifying location of said ultrasound transducer;
 a control unit for controlling said ultrasound transducer and processing data signals received from said ultrasound transducer;
 means for transmitting a signal from said ultrasound transducer to said control unit; and
 means for displaying tissue thickness parameters received from said control unit, wherein said ultrasound transducer is configured to operate at two or more frequencies and wherein the ratio of scattered signal at different frequencies can be used to estimate water-fat content.

26. The system of claim 1, wherein said ultrasound transducer is battery powered.

27. A system for mapping tissue layer thickness, comprising:
 an ultrasound transducer for producing ultrasound energy;
 means for coupling said ultrasound energy to skin;
 means for identifying location of said ultrasound transducer;
 a control unit for controlling said ultrasound transducer and processing data signals received from said ultrasound transducer;
 means for transmitting a signal from said ultrasound transducer to said control unit; and
 means for displaying tissue thickness parameters received from said control unit, wherein said control unit comprises software that is adapted to read and analyze data from said ultrasound transducer, wherein said software is adapted to calculate change in fat layer thickness during the course of a liposuction procedure for display by said means for displaying tissue thickness parameters.

28. The system of claim 27, wherein said software is adapted to produce a table of tissue thickness parameters for display by said means for displaying tissue thickness parameters.

29. The system of claim 27, wherein said software is adapted to produce a color-coded anatomical map for display by said means for displaying tissue thickness parameters.

30. The system of claim 1, wherein said control unit comprises an interface selected from the group consisting of a keyboard, a mouse and a touch screen.

31. The system of claim 1, wherein said ultrasound transducer comprises a curvature.

32. The system of claim 1, wherein said ultrasound transducer comprises an operating frequency within in the range from about 500 kHz to 10 MHz.

33. The system of claim 1, wherein said means for coupling said ultrasound transducer to skin comprises an acoustic matching segment within a disposable plastic container, wherein said ultrasound transducer may be operatively connected to said acoustic matching segment.

34. The system of claim 1, further comprising a disposable plastic container with an acoustic matching segment therein, wherein said means for coupling said ultrasound transducer to skin is operatively connected to said acoustic matching segment.

35. A method for producing a tissue layer thickness map for use in guiding a liposuction procedure, comprising:
 (i) contacting an ultrasound transducer to the skin tissue of a human;
 (ii) coupling ultrasound waves from said ultrasound transducer into and through said skin tissue;
 (iii) detecting reflected ultrasound waves from various tissue layers and interfaces at and beneath said skin tissue to produce a detected ultrasound signal;
 (iv) identifying and recording the location of said ultrasound transducer on said skin tissue;
 (v) analyzing said detected ultrasound signal to calculate the time lapse between transmission of said ultrasound waves and reflection of said reflected ultrasound waves from various tissue layers and interfaces at and beneath said skin tissue;
 (vi) calculating a tissue thickness value from said time lapse;
 (vii) repeating steps (i)–(vi) to obtain a plurality of tissue thickness values at a plurality of locations on said skin;
 (vii) producing a map of said tissue thickness values; and
 (viii) using said map to guide a liposuction procedure.

36. The method of claim 35, further comprising analyzing the reflected signal amplitude from each tissue layer of said various tissue layers to determine tissue composition.

37. The method of claim 35, further comprising using multiple ultrasound transducers that probe adjacent regions to improve signal to noise.

38. The method of claim 37, where said multiple ultrasound transducers operate at different frequencies.

* * * * *